United States Patent [19]

Lerch et al.

[11] 3,961,062

[45] June 1, 1976

[54] PHARMACEUTICAL COMPOSITION CONTAINING 1-(IMIDAZOLE-1-YL)-ISOQUINOLINES AND METHOD OF TREATING HYPERLIPEMIA

[75] Inventors: Ulrich Lerch, Hofheim, Taunus; Ernold Granzer, Kelkheim, Taunus, both of Germany

[73] Assignee: Hoechst Aktiengesellschaft, Frankfurt am Main, Germany

[22] Filed: Mar. 26, 1975

[21] Appl. No.: 562,048

Related U.S. Application Data

[62] Division of Ser. No. 454,713, March 25, 1974, Pat. No. 3,914,236.

[30] Foreign Application Priority Data

Mar. 26, 1973 Germany............................ 2314918

[52] U.S. Cl. ............................................... 424/258
[51] Int. Cl.² ........................................ A61K 31/47
[58] Field of Search .................................. 424/258

[56] References Cited
FOREIGN PATENTS OR APPLICATIONS
7,445M 1/1970 France ............................... 424/258

*Primary Examiner*—Frederick E. Waddell
*Attorney, Agent, or Firm*—Curtis, Morris & Safford

[57] ABSTRACT

This application discloses pharmaceutical compositions containing, and a method of treatment with, 1-(1-imidazolyl)-isoquinolines of the general formula I and their physiologically tolerated salts,

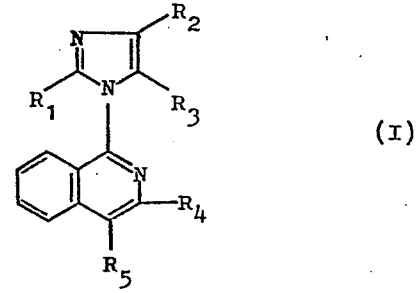

(I)

in which $R_1$, $R_2$ and $R_3$ represent hydrogen, alkyl of 1 to 4 carbon atoms or phenyl, $R_1$, $R_2$ and $R_3$ may be identical or different, $R_4$ represents hydrogen, alkyl of 1 to 4 carbon atoms, phenyl or chlorine, and $R_5$ represents hydrogen, alkyl of 1 to 6 carbon atoms, cycloalkyl of 5 to 8 carbon atoms, phenyl or chlorine.

18 Claims, No Drawings

PHARMACEUTICAL COMPOSITION CONTAINING 1-(IMIDAZOLE-1-YL)-ISOQUINOLINES AND METHOD OF TREATING HYPERLIPEMIA

This is a division, of application Ser. No. 454,713 filed Mar. 25, 1974 now U.S. Pat. No. 3,914,236.

The present invention provides 1-(imidazole-1-yl)-isoquinolines of the general formula I

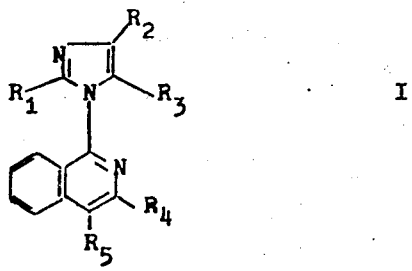

in which $R_1$, $R_2$ and $R_3$ represent hydrogen, alkyl of 1 to 4 carbon atoms or phenyl, and in which $R_1$, $R_2$ and $R_3$ may be identical or different, $R_4$ represents hydrogen, alkyl of 1 to 4 carbon atoms, phenyl or chlorine, and $R_5$ represents hydrogen, alkyl of 1 to 6 carbon atoms, cycloalkyl of 5 to 8 carbon atoms, phenyl or chlorine, and their physiologically tolerated salts.

The compounds of the above-specified formula I have an action on the metabolism and may therefore be used as medicaments.

The invention furthermore provides a process for preparing the above-specified compounds and also pharmaceutical preparations of these compounds.

The process for preparing the compounds of the invention reacts compounds of the general formula II

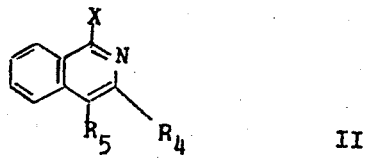

in which $R_4$ and $R_5$ have the meanings given above, and X represents a halogen atom, preferaby chlorine, with substituted imidazoles of the formula III

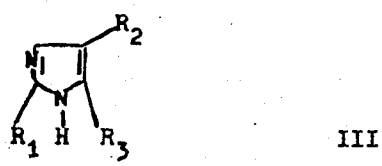

in which $R_1$ to $R_3$ have the meaning given above, or with their reactive derivatives.

Suitable starting compounds of the formula II are especially those in which X is a chlorine atom. The 1-chloro-isoquinolines are accessible according to various methods, of which some will be mentioned hereinafter:

1-chloro-isoquinolines of the general formula II can be prepared, for example by transforming isoquinolines which are unsubstituted in 1-position with hydrogen peroxide in glacial acetic acid or with per-acids such as m-chloro-perbenzoic acid into the corresponding N-oxides which, when heated with phosphoroxychloride, react to yeild the desired 1-chloro-isoquinolines. Reactions of this kind are described, for example in J. Am. Pharm. Sci. Ed. 41, 643 (1952) and are particularly suited for the preparation of 1-chloro-isoquinolines which are substituted byb alkyl in the 3 and/or 4-position.

1-Chloroisoquinolines of the formula II, in which $R_4$ represents a chlorine atom and $R_5$ represents hydrogen, alkyl or phenyl, can be prepared, for example by heating homophthalic acid imides with phosphoric acid phenyl ester dichloride (Chem. Ber. 103, 1960 (1970)) or with phosphoroxy chloride (Ber. dtsch. chem. Ges. 33, 980 (1900)). A further method of preparing them is the "one-pot" process described in Chem. Ber. 102, 3666 (1969). In this process, 2-oximinoindane-1-one is reacted with an excess of phosphorus pentachloride in the presence of anhydrous hydrogen chloride. The 3-chloro-2H-isoquinoline-1-ones formed as intermediate products may also be isolated and reacted separately to yield the 1-chloro-isoquinolines.

The preparation of 1-chloro-isoquinolines of the formula II may be effected also by heating the correspondingly substituted 2H-isoquinoline-1-ones of the formula IV

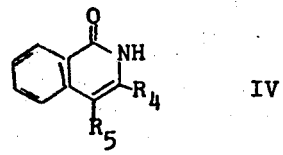

with phosphoric acid chlorides such as phosphoroxy chloride (J. Am. Chem. Soc. 71, 937 (1949)), phosphorus pentachloride or according to the method described in Chem. Ber. 103, 1960 (1970) with phosphoric acid phenyl ester dichloride.

1-Chloro-iosquinolines of the formula II, in which $R_4$ is hydrogen, alkyl or phenyl and $R_5$ is a chlorine atom, can be prepared from corresponding 2-H-isoquinoline-1-ones which are unsubstituted in 4-position by heating with at least 2 moles of phosphorus pentachloride (Ber. dtsch. chem. Ges. 18, 3470 (1885)).

The 2H-isoquinoline-1-ones of the formula IV required for the preparation of the 1-chloro-isoquinolines can be prepared by several methods described in the literature, for example according to the methods described in J. Am. Pharm. Assoc. Sci. Ed. 41, 643 (1952) Chim. Ther. 4, 469 (1970), J. Org. Chem. 16, 1960 (1970). For the preparation of the imidazoles of the formula III; there may be used several methods, for example the methods described in Ber. dtsch. Ges. 70, 570 (1937), Chem. Ber. 86, 96 (1953), Chem. Ber. 86, 88 (1953), Soc. 115, 227 (1919) or in Elderfield, Heterocyclic Compounds, Vol. 5, on pages 209 to 223.

With regard to reaction conditions, the process of the invention can be largely varied and adapted to the prevailing circumstances. The reactions may be carried out in absence or in the presence of solvents at room temperature or at an elevated temperature. It is preferred to carry out the reactions at temperatures in the range of from 50° and 150° C.

As solvents there may be used: aromatic and aliphatic hydrocarbons such as petroleum ether, cyclohexane, benzene and toluene, halogeno-alkanes such as carbon tetrachloride, chloroform, tetrachloroethane or tetrachloroethylene, open chain and cyclic ethers such as dialkyl ethers, glycol-dialkyl ethers, diglycol-dialkyl ethers, tetrahydrofurane, dioxane, dialkyl ketones and cyclic ketones such as acetone and cyclohexanone, primary, secondary and tertiary alcohols, esters, acetonitrile, as well as aprotic solvents such as diemthylformamide, dimethylacetamide, N-methyl-pyrrolidone, dimethyl sulfoxide and hexamethyl-phosphoric acid triamide.

The reaction of the imidazoles of the formula II with the isoquinolines of the formula II is advantageously effected in the presence of a base. As bases, there may be used alkali metal hydroxides, alkali metal carbonates and alkali metal hydrogenocarbonates, organic bases such as tertiary amines, pyridine and an excess of imidazole of the formula III.

The process of the invention may also be carried out by reacting the isoquinolines of the formula II with reactive derivatives, for example metallo-organic derivatives of the imidazoles of the formula III. For preparing the metallo-organic imidazole compounds, there are suitable, for example alkali metal hydrides, alkyl-metallo-amides, alkali metal organyls and methyl-, butyl- or phenyl-lithium and alkyl- and arylmagnesium halides.

Especially preferred are those compounds of the formula I in which $R_1$, $R_2$ and $R_3$ are identical or different and represent hydrogen, methyl or phenyl. Besides chlorine, $R_4$ represents in particular hydrogen and among the definitions given for $R_5$, it is preferred to use hydrogen, alkyl and phenyl.

The transformation of the free compounds into the physiologically tolerated salts is effected according to known methods with organic or inorganic acids, for example hydrochloric acid, sulfuric acid, phosphoric acid, lactic acid, tartaric acid or oxalic acid.

1(Imidazole-1-yl)-isoquinolines of the formula I and processes for preparing them have not been known hitherto.

In addition to the compounds mentioned in the Examples, there may be prepared, preferably, the following further compounds:

3-chloro-1-(2-methyl-imidazole-1-yl)-isoquinoline
3-chloro-1-(2-ethyl-imidazole-1-yl)-isoquinoline
3-chloro-1-(2-phenylimidazole-1-yl)-isoquinoline
3-chloro-1-(4-phenylimidazole-1-yl)-isoquinoline
3-chloro-1(4,5-dimethyl-imidazole-1-yl)-isoquinoline
3-chloro-1-(4,5-diethylimidazole-1-yl)-isoquinoline
3-chloro-1-(4,5-di-n-propylimidazole-1-yl)-isoquinoline
3-chloro-1(4,5-di-n-butyl-imidazole-1-yl)-isoquinoline
3-chloro-1-(4,5-diphenyl-imidazole-1-yl)-isoquinoline
3-(chloro-1(1-imidazolyl)-4-methyl-isoquinoline
3-chloro-1-(1-imidazolyl)-4-ethyl-isoquinoline
3-chloro-1-(1-imidazolyl)-4-n-propyl-isoquinoline
3-chloro-1-(1-imidazolyl)-4-sec. propyl-isoquinoline
3-chloro-1-(1-imidazolyl)-4-n-butyl-isoquinoline
3-chloro-1-(1-imidazoyl)-4-sec. butyl-isoquinoline
3-chloro-1-(1-imidazolyl)-4-(n-pentyl-1)-isoquinoline
3-chloro-1-(1-imidazolyl-4-(n-pentyl-2)-isoquinoline
3-chloro-1-(1-imidazolyl)-4-(n-pentyl-3)-isoquinoline
3-chloro-1-(1-imidazolyl)-4l-(3-methyl-n-butyl-1)-isoquinoline
3-chloro-1-(1-imidazolyl)-4-n-hexyl-isoquinoline
3-chloro-1-(1-imidazolyl-4-(n-hexyl-2)-isoquinoline
3-chloro-1-(1-imidazolyl)-4-(n-hexyl-3)-isoquinoline
3-chloro-1-(1-imidazolyl)-4-(4-methyl-n-pentyl-1)-isoquinoline
3-chloro-4-phenyl-1-(2-ethyl-imidazole-1-yl)-isoquinoline
3-chloro-4-phenyl-1-(2-n-propyl-imidazole-1-yl)-isoquinoline
3-chloro-4-phenyl-1-(2-n-butyl-imidazole-1-yl)-isoquinoline
3-chloro-4-phenyl-1-(4-methyl-imidazole-1-yl)-isoquinoline
3-chloro-4-phenyl-1-(4-ethyl-imidazole-1-yl)-isoquinoline
3-chloro-4-phenyl-1-(4-n-propyl-imidazole-1-yl)-isoquinoline
3-chloro-4-phenyl-1-(4-n-butyl-imidazole-1-yl)-isoquinoline
3-chloro-4-phenyl-1-(4,5-diethyl-imidazole-1-yl)-isoquinoline
3-chloro-4-phenyl-1-(4,5-di-n-propyl-imidazole-1-yl)-isoquinoline
3-chloro-4-phenyl-1-(4,5-di-n-butyl-imidazole-1-yl)-isoquinoline
3-chloro-4-phenyl-1-(2-methyl-4-phenyl-imidazole-1-yl)-isoquinoline
3-chloro-4-phenyl-1-(2-ethyl-4-phenyl-imidazole-1-yl)-isoquinoline
3-chloro-4-phenyl-1-(2-phenyl-4-methyl-imidazole-1-yl)-isoquinoline
3-chloro-4-phenyl-1-(2,4-diphenyl-imidazole-1-yl)-isoquinoline
1-(1-imidazolyl)-4-methyl-isoquinoline
1-(1-imidazolyl)-4-n-propyl-isoquinoline
1-(1-imidazolyl)-4-sec. propyl-isoquinoline
1-(1-imidazolyl)-4-sec. butyl-isoquinoline
1-(1-imidazolyl)-4-(n-phenyl-1)-isoquinoline
1-(1-imidazolyl)-4-(n-pentyl-2)-isoquinoline
1-(1-imidazolyl)-4-(n-pentyl-3)-isoquinoline
1-(1-imidazolyl)-4-(3-methyl-butyl-2-isoquinoline
1-(1-imidazolyl)-3-methyl-isoquinoline
1-(1-imidazolyl)-3-n-propyl-isoquinoline
1-(1-imidazolyl)-3-n-butyl-isoquinoline
1-(1-imidazolyl)-4-chloro-3-methyl-isoquinoline
1-(1-imidazolyl)-4-chloro-3-n-propyl-isoquinoline
1-(1-imidazolyl)-4-chloro-3-n-butyl-isoquinoline.

The compounds of the invention have valuable therapeutic properties. They lower the level of lipids in the serum and may therefore be used for the therapy of primary hyperlipemias and also of certain secondary hyperlipemias, for example in the case of diabetes, in which cases the favorable effect on the metabolic conditions regarding diabetes is accompanied by a hypoglycemic activity of these compounds.

Since increased hyperlipemidia is the most dangerous cause of coronary heart diseases and elevated serum lipid values involve the great risk of causing arteriosclerotic diseases of different localisation, not only in the area of the coronary vessels, the reduction of elevated serum lipid levels is extremely important in the prophylaxis and therapy of atheroscleroris, especially in the area of the coronary vessels. Since the compounds of the invention described above are capable of lowering normal and elevelated serum lipid levels in animals, they are suitable for the treatment of arteriosclerotic diseases in particular in the area of the coronary vessels, but also of other blood vessels.

The hypolipidemic activity of the above-specified compounds was verified by the following tests:

1. Male rats with normal serum lipid content. The values given in Table 1 indicate the changes of the concentration of certain classes of lipids in the serum after 8 day's treatment with the dosages indicated. Administration was effected perorally with the aid of an esophagal sound. Blood was withdrawn in general prior to and after the treatment and the concentration of cholesterol was determined according to the method of Lauber and Richterich and that of triglycerides was determined according to the method of Eggstein and Kreutz. In the Examples indicated in the following Tables, the changes of serum lipid caused by the treatment with the substances are defined as follows:
   a. the percentual changes of the group treated, referred to the initial value of the group treated, the initial value being 100%, and
   b. the change of the posterior value of the group treated with reference to the posterior value of a simultaneously observed control group (placebo group), the placebo group being postulated as being 100%. Thus, the value indicated before the dash represents the percentage change with regard to the initial value, the value after the dash represents the percentage change of the group treated with the preparations, referred to the placebon group.

2. Hypertriglyceridemia induced by carbohydrates and caused by administration of fructose of male rats. It is strongly reduced by a 3 day's peroral pretreatment with the indicated substances, as shown by the comparison with the placebo group (Table 2).

3. Dietetic-medicamentous hypercholisterinemia of the male rat

From the 3rd administration of the preparations on, all animals were fed with a diet enriched with 2% of chloesterol, 2% of sodium cholate, 0.3% of methyl-thiouracil, 20% l coconut fat and 44% of cane sugar.

The serum lipid concentration of the animals treated with the indicated compounds was compared with that of a placebo group and under the same dietetic conditions. Experience has shown that the diet indicated causes within one week and increase of the concentration of cholesterol in the serum to about ten times of its initial value and that of the serum triglycerides to three time of its initial value. The compounds indicated were administered once daily with the esophagal sound to groups of rats comprising 10 animals each. The percentage reduction of the serum lipid concentration, referred to that of a placebo group (merely diet, without any preparation) is indicated in Table 3.

4. Dietetic hypercholesteremia of the male rat

All animals were fed with a diet enriched with 2% of chloesterol and 20% of coconut fat. The concentrations of lipids in the serum of the animals treated with compounds was compared with those of an untreated control group (placebo group) standing under the same diet. (Table 4).

5. Triton hyperlipidemia of the male rat

The influence of a 4 day's pre-treatment with the compounds indicated on the hyperlipidemia caused by an i.p. administration of 300 mg/kg of Triton$^{(R)}$ WR 1339 was compared with that caused by Triton on a placebo group (Table 5).

6. Dietetic hypercholesterinemia of the rabbit

With the first administration of the preparations, rabbits were given a diet ad libitum which contained 2% of cholesterol and 20% of coconut fat. The increase of the cholesterol in the serum (up to 20 times the normal value) which takes place as a consequence of this diet was inhibited or timely delayed by the preparations administered once daily with an esophagal sound. The percentual inhibition was calculated from a comparison with a placebo group under same diet conditions (Table 6).

The favorable action of the compounds of the formula I on diabetically caused disorders of the metabolism, especially with obese and over-weight patients, is not only due to a normalization of the disturbed lipid metabolism, thus to the hyperlipidemic action, but also to an action on the carbohydrate metabolism.

The blood sugar lowering action was determined as follows:

1. By the change of the serum sugar of normal male rats, which had been fasted for 20 hours, after an 8-day treatment with the indicated compounds in comparison to a placebo group. The determination of the serum sugar was effected with an autoanalyser (Table 7). 2. By the influence on the blood sugar of male rats, which were under gluco-neogenetic condition of the metabolism; this condition was produced by 44 hours of hunger and intraperitoneal additional administration of 10 mg/kg of prednisolone 24 hours before the blood withdrawal. The administration of the indicated compounds was effected once per day orally with the esophagal sound on 9 days preceding the blood withdrawal and additionally 3 hours before the withdrawal of blood. Comparison was made with a placebo group. The determination of the sugar in the serum was carried out with the aid of an auto-analyzer (Table 8).

3. By the change of glucose in the blood caused by the indicated preparations (in comparison to the placebo group) in male rats which, after a 3 day's administration of the indicated compounds, had been challenged with fructose. The determination of glucose in the blood was carried out according to the hexokinase method directly in the hemolystate (Table 9).

The new compounds may be used either alone or in admixture with physiologically tolerated carriers. The form of oral administration is preferred. In this respect, the active substances are mixed with known substances and transformed by known methods into forms that are suited for administration, for example tablets, capsules, aqueous or oily suspensions or aqueous or oily solutions. As inert carriers, there may be used, for example magnesium carbonate, lactose or maize starch, with the addition of other substances, for example magnesium stearate. The preparation may effected in such a manner to obtain a dry or wet granulate. As oily carriers or solvents, there may be used in particular vegetable or animal oils such as sunflower oil or fish-liver oil. As single dose, there may be administered about 3 to 200 mg/kg per day.

A particular application of the compounds of the invention comprises their combination with other active substances. Such other active substances comprise, among others, antidiabetic agents such as Glycodiazine, Tolbutamide, Glibenclamide, Phenformine, Buformine, Metformine, or agents having an action on the blood circulation in a large sense, especially however dilatators of the coronary vessels such as Chromonar or phrenylamine and blood pressure lowering agents such as Reserpine, α-methyl-Dopa or Clonidine, other agents lowering the lipid level or geriatric agents, psychopharmaceutic agents such as Chlorodiazepoxide, Diazepam or Meprobramate as well as vitamins.

Table 1

| Compound of examples | changes after 8 oral administrations of mg/kg/day to a normolipemic male rat | | | | | |
|---|---|---|---|---|---|---|
| | 100 | | 30 | | 10 | |
| | Serum Cholesterol | Serum Triglycerides | Serum Cholesterol | Serum-Triglycerides | Serum Cholesterol | Serum Triglycerides |
| 1 | −22/−10 | −69/−58 | −12/−9 | | − 3/− 5 | −25/−27 |
| 2 | | −62/−62 | | −21/−17 | | |
| 10 | −10/−17 | −66/−54 | | | /−23 | /−23 |
| 11 | | −72/−42 | | | | −20/−36 |
| 15 | | −57/−55 | −21/−17 | −33/−29 | | −21/−14 |
| 3 | −26/−43 | −30/−24 | | | −15/− 8 | |
| 7 | | | −41/−31 | −18/−14 | −17/−13 | |
| 6 | | | −22/−25 | −21/−23 | | |
| 13 | | −20/−22 | | | | |
| Clofibrat | −25/−17 | −21/−15 | − 8/− 6 | −15/−10 | ineffective | |
| | | 3 mg/kg/day | | 1 mg/kg/day | | 0,3 mg/kg/day |
| 1 | − 1/ | −42/−26 | −10/− 6 | −60/−20 | | −16/−50 |

Table 2

Carbohydrate induced Hypertriglyceridemia
% changes after challenge with fructose and 3 oral administrations of mg/kg/day to a male rat

| Dose compound of example | 100 | | 30 | | 10 | |
|---|---|---|---|---|---|---|
| | Serum Cholesterol | Serum Triglycerides | Serum Cholesterol | Serum Triglycerides | Serum Cholesterol | Serum Triglycerides |
| 11 | | −76 | | | −38 | −43 |
| 2 | | −79 | | −71 | | −49 |
| 10 | | | −30 | −79 | | |
| 15 | | −93 | | −75 | | |
| 3 | −20 | −70 | | | | |
| Clofibrat | | −34 | | −20 | ineffective | |

Table 3

Antihyperlipidemic action on male rats, in which starting with 3rd administration of the preparations, a hyperlipidemia was dietetically-medicamentously induced. Comparison with a placebo group.

| Compound | mg/kg/day | % change of Serum total cholesterol after days | | Serum-triglycerides after days | |
|---|---|---|---|---|---|
| | | 7 | 14 | 7 | 14 |
| Example 1 | 100 | −62 | −24 | + 9 | −52 |
| | 10 | −19 | +13 | +12 | −19 |
| Clofibrat | 100 | −12 | − 7 | −15 | − 4 |

Table 4

Antihyperlipidemic action on male rats, which starting with the administration of the preparations, were offered a diet enriched with 2 % of cholesterol and 20 % of coconut fat. Comparison with a placebo group.

| Compound | mg/kg/day | % change of serum cholesterol after days | | | | | |
|---|---|---|---|---|---|---|---|
| | | 10 | 15 | 24 | 31 | 38 | 45 |
| from example 1 | 33 | −15 | −45 | −26 | −20 | −25 | −22 |
| | 10 | +10 | −28 | −19 | | − 9 | − 5 |
| | 3.3 | + 2 | −30 | −19 | − 4 | −19 | −12 |
| Clofibrat | 100 | − 3 | − 4 | + 4 | +35 | +11 | +32 |
| | | % change of serum-triglycerides | | | | | |
| from example 1 | 33 | −32 | −37 | −22 | −16 | −26 | −35 |
| | 10 | −31 | −18 | −24 | − 7 | − 9 | −35 |
| | 3.3 | −15 | −28 | − 24 | −15 | − 6 | −35 |
| Clofibrat | 100 | − 5 | −42 | −11 | −11 | +10 | −26 |

Table 5

TRITON — hyperlipidemia of the male rat

| | Dose mg/kg/day | Serum Total cholesterol mg/100 ml X̄ | % change against control | Serum-Triglycerides mMol/l X̄ | % change against control |
|---|---|---|---|---|---|
| Control | — | 510 | | 42.43 | |
| Compound of example 1 | 100 | 307 | −40 | 36.68 | −14 |
| | 30 | 436 | −15 | 32.28 | −24 |
| Clofibrat | 100 | 364 | −29 | 35.56 | −16 |

Table 6

Inhibiting action on the formation of a hypercholesterinemia in rabbits, which obtained beginning with the first application, of the preparations, a diet enriched with 2 % of cholesterol and 20 % of coconut fat. Comparison with placebo group held under the same diet.

| Compound | mg/kg/day | % change of serum cholesterol after days | | | | | |
|---|---|---|---|---|---|---|---|
| | | 10 | 17 | 24 | 31 | 38 | 46 |
| of example 1 | 10 | −40 | −27 | − 8 | −33 | −8 | |
| Clofibrat | 100 | −32 | −37 | −24 | −18 | +16 | |

Table 7

% change of serum sugar (autoanalyzer) after 8 oral administrations to the male rat with mg/kg/day

| Compound of example | 100 | 30 | 10 |
|---|---|---|---|
| 10 | −46/−42 | | |
| 13 | −41/−43 | | |
| 5 | −12/−35 | | |
| 6 | | | −21/−48 |
| 17 | | −12/−11 | |
| Phenformin | /−10 | | |

Table 8

% change of serum sugar (autoanalyzer) after 10 oral administrations on a fasted prednisolone-rat with mg/kg/day

| | 100 |
|---|---|
| Compound of Example 13 | −13 |
| Phenformin | − 7 |

Table 9

% change of blood glucose (hexokinase method) in a male rat challenged with fructose after 8 peroral administrations in comparison to a placebo group.

| Compound of Example | 100 mg/kg/day | 30 mg/kg/day |
|---|---|---|
| 2 | | −12 |
| 10 | −45 | −22 |
| 15 | −31 | − 7 |
| 3 | − 9 | |

The following Examples illustrate the invention:

EXAMPLE 1:

3-Chloro-1-(1-imidazolyl)-4-phenylisoquinoline hydrochloride a. 3-Chloro-4-phenyl-2H-isoquinoline-1

22.9 g. (0.11 mole) of phosphorus pentachloride were introduced into a suspension of 23.7 g (0.1 mole) of 2-oximo-3-phenyl-indanone-1 in 200 ml of carbon tetrachloride while stirring and in such a manner that the solvent was brought to boiling. After having stirred for 4 hours at room temperature, a mixture of 20 ml of methanol and 5 ml of water was added dropwise and the whole was allowed to stand for 24 hours. The reaction mixture was evaporated under reduced pressure and the residue was heated with 100 ml of methanol for 1 hour under reflux. After cooling, the product was filtered off with suction, washed with a small amount of methanol and recrystallized from methanol. Colorless crystals were obtained. M.p. 276° to 278° C.

b. 1,3-Dichloro-4-phenylisoquinoline 100 g (0.39 mole) of crude 3-chloro-4-phenyl-2H-isoquinoline-1 were heated for 4 hours to 150° C in an autocalve in a mixture of 400 ml of $POCl_3$ and 5Ml of concentrated hydrochloric acid. After concentration of the reaction solution under reduced pressure, the remaining oil was poured on ice and brought to crystallization by the addition of seed crystals. After recrystallization from petroleum ether (60° to 90° C), the product was found to melt at 94° to 95° C.

1,3-Dichloro-4-phenylisoquinoline could also be prepared by heating equal quantities by weight of 3-chloro-4-phenyl-2H-isoquinoline-1 and phosphorus pentachloride for 4 hours to 140° to 150° C and removing at the same time by distillation the phosphoroxy chloride that had formed. The excess of phosphorus pentachloride was hydrolyzed with ice, the product was dissolved in chloroform, washed with water and, after removal of the solvent it was recrystallized from petroleum ether.

c. 3-Chloro-1-(1-imidazolyl)-4-phenyl-isoquinoline 15 g (0.5 mole) of an 80% suspension of sodium hydride in mineral oil were introduced, while stirring, into a solution of 37.5 g (0.6 mole) of imidazole in 250 ml of absolute 1,2-dimethyoxyethane. The whole was heated for 30 minutes to the boil and then a solution of 109.6 g (0.4 mole) of 1,3-dichloro-4-phenylisoquinoline in 100 ml of absolute 1,2-dimethoxyethane was added dropwise. The mixture was then boiled for 3 hours under reflux, the solvent was distilled off under reduced pressure and the residue was dissolved in a mixture of methylene chloride and water. The organic phase was washed with water, the sol-was removed under reduced pressure and the product was recrystallized from toluene. M.p. 165° to 168°.

Hydrochloride:

40 g of the base were dissolved in a small amount of warm methylene chloride and the solution was diluted with a four-fold quantity of benzene. Upon addition of ethereal HCl and trituration, the hydrochloride precipitated. Recrystallization in methylene chloride/benzene. M.p. > 195° C Phosphate:

A concentrated solution of the base in acetone was combined with a solution of the 1.1-molar amount of crystallized phosphoric acid in a small amount of acetone. The phosphate crystallized upon standing. M.p. 175 to 177° C.

e. 3-Chloro-1-(1-imidazolyl)-4-phenylisoquinoline 2.74 g (10 mmoles) of 1,3-dichloro-4-phenylisoquinoline abd 2.04 g (30 mmoles) of imidazole were heated for 3 hours to 150° C in 5 ml of dimethyl-formamide. Working up was effected as described uner 1d.

f. 3-Chloro-1-(imidazolyl)-4-phenylisoquinoline 2.74 g (10 moles) of 1,3-dichloro-4-phenylisoquinoline, 1.02 g (15 mmoles) of imidazole and 2.7 g (15 mmoles) of tri-n-butylamine were heated for 18 hours in 5 ml of dioxane under reflux. Working was carried out as described under 1c.

g. 3Chloro-1-(1-imidazolyl)-4-phenylisoquinoline 2.74 g (10 mmoles) of 1,3-dichloro-4-phenylisoquinoline, 1.02 g (15 mmoles) of imidazole and 5 ml of pyridine were heated for 8 hours under reflux and, after cooling, distributed between benzene and water. The residue which remained behind after evaporation of the organic phase was chromagtographed on silica-gel. As solvent, a mixture of chloroform and methanol 95:5 was found to be suitable.

EXAMPLE 2:

3-Chloro-1(1-imidazolyl)-isoquinoline

Reaction analogous to that of 1c., from 1,3-dichlorosioquinoline. M.p. 160° to 161° C.
Hydrochloride: M.p. 251° C.

EXAMPLE 3:

3-Chloro-1-(2-methylimidazole-1-yl)-4-phenylisoquinoline

Reaction analogous to that of 1c. with 2-methylimidazole. M.p. 167° to 168° C.
Hydrochloride: M.p. 231° to 232° C.

EXAMPLE 4:

3-Chloro-1-(4-phenylimidazole-1-yl)-4-phenylisoquinoline hydrochloride

Reaction analogous to that of 1c, with 4(5)-phenylimidazole. M.p. 255° to 257° C.

EXAMPLE 5:

3-Chloro-(2-phenylimidazole-1-yl)-4-phenylisoquinolineoxalate 870 mg (29 mmoles) of an 80% suspension of sodium hydride in mineral oil were added portionwise to 4.3 g (30 mmoles) of 2-phenylimidazole in 50 ml of absolute dioxane and the whole was heated to 50° to 60° C until the evolution of hydrogen was finished. Then, 7.1 g (26 mmoles) of 1,3-dichloro-4-phenyl-isoquinoline were added and, after having evaporated the solvent, the reaction mixture was heated for 7 hours to 140° – 150° C. The reaction mixture was distributed between chloroform and water. The organic phase was dried and evaporated. The product was purified by column chromatography on silicagel with chloroform/ethyl acetate 8:2. It was dissolved in isopropanol and the oxalate was precipitated with a solution of 1.6 g. of oxalic acid in isopropanol. Finally, it was recrystallized from ethanol. M.p. 192° to 194° C (decomp.).

EXAMPLE 6:

3-Chloro-1-(4,5-dimethylimidazole-1-yl)-4-phenylisoquinoline

Reaction analogous to 5, with 4,5-dimethylimidazole. M.P. 164° to 165° C.
Hydrochloride: M.p 264° to 265° C.

EXAMPLE 7:

3-Chloro-1-(4,5-diphenylimidazole-1-yl)-4-phenylisoquinoline

Reaction analogous to 5, with 4,5-diphenylimidazole. M.p. 195° to 196° C.

EXAMPLE 8:

1-(1-Imidazolyl)-4-cyclohexylisoquinoline a. 4-Cyclohexyl-3,4-dihydro-2H-isoquinoline-1-one 195 g (0.71 mole) of N-(2-cyclohexyl-2-phenyl-ethyl)-carbamide acid ethyl ester were introduced, while stirring, to 1800 g of polyphosphoric acid, at 130° C, in such a manner that the internal temperature was 130° to 140° C. The temperature was kept for 30 minutes at 140° C. After cooling to about 70° C, the reaction mixture was poured on ice and allowed to stand overnight. The product was filtered off with suction and distributed between water and chloroform. The organic phase was washed with water and saturated sodium bicarbonate solution, dried and evaporated. The residue was recrystallized from ethanol. M.p. 156° to 157° C.

b. 4-Cyclohexyl-2H-isoquinoline-1-one 50 g of 4-cyclohexyl-3,4-dihydro-2H-isoquinoline-1-one and 20 1 g of methanol-wet 30% Pd/C were heated while to 220° C in a stream of argon. Thin-layer chromatographic analysis revealed that the reaction was practically completed after 75 minutes. The product was dissolved in chloroform, the catalyst was separated and the organic phase was evaporated. After recrystallization from acetone, colorless crystals were obtained. M.p. 111° to 112° C c. 1-Chloro-4-cyclohexylisoquinoline 40.7 g (0.18 mole) of 4-cyclohexyl-2H-isoquinoline-1-one and 340 g (2 moles) of phosphoroxy chloride were heated for 5 hours under reflux. The excess $POCl_3$ was removed under reduced pressure, the residue was poured on ice and the product was extracted with benzene. The organic phase was washed with water, dried with magnesium sulfate and evaporated. The residue was recrystallized from petroleum ether with the aid of active carbon. M.p. 53° to 55°C.

d. 1-(1-Imidazolyl)-4-cyclohexylisoquinoline.

3.4 g (50 mmoles) of imidazole were allowed to react with 1.9 g (49 mmoles) of sodium amide in 50 ml of absolute dioxane until the evolution of ammonia was finished. Then 9 g (37 mmoles) of 1-chloro-4-cyclohexyl-isoquinoline were added and the solvent was evaporated. The reaction mixture was heated for 3 hours to 140° C, distributed between methylene chloride and water and the organic phase was evaporated after having been dried over magnesium sulfate. The oily crude product was taken up in 30 ml of ether and crystallized upon trituration. M.p. 92° to 93° C, hydrochloride M.p. 228° to 229° C.

EXAMPLE 9:

1-(4-phenylimidazole-1-yl)-4-cyclohexyl-isoquinoline

Reaction analogous to 5, with 4(5)-phenyl-imidazole and 1-chloro-4-cyclohexylisoquinoline, M.p. 169° to 170° C.

Dihydrochloride: M.p. 192° to 194° C.

EXAMPLE 10:

4-Ethyl-1-(1-imidazolyl)-isoquinoline hydrochloride a. e-Ethyl-3,4-dihydro-2H-isoquinoline-1-one:
Reaction analogous to 8a, from N-(2-phenylbutyl)-carbamic acid ethyl ester, B.p.$_{0.9}$159° to 164° C.

b. 4-Ethyl-2H-isoquinoline-1-one:
Reaction analogous to 8 b from 4-ethyl-3,4-dihydro-2H-isoquinolinel-one, M.p. 133° to 134° C.

c. 4-Ethyl-1-chloroisoquinoline:
Reaction analogous to 8 c, but from 4-ethyl-2H-isoquinoline-1-one, B.p.$_{0.1}$ 98° to 100° C.

d. 4-Ethyl-1-(1-imidazolyl)-isoquinoline hydrochloride:
Reaction analogous to 8d., from 4-ethyl-1-chloroisoquinoline, M.p. 208° to 290° C.

EXAMPLE 11:

4-n-Butyl-1-(1-imidazolyl)-isoquinoline a. 4-n-Butyl-23,4-dihydro-2H-isoquinoline-1-one:
Reaction analogous to 8a., from N-(2-phenyl-n-hexyl)-carbamic acid ethyl ester, B.p.$_{0.6}$ 164° to 168° C.

b. 4-n-Butyl-2H-isoquinoline-1-one:
Reaction analogous to 8b., from 4n-butyl-3,4-dihydro-2H-isoquinonline, M.p. 92° to 95° C.

c. 4-n-butyl-1-chloroisoquinoline:
Reaction analogous to 8c., from 4-n-butyl-2H-isoquinoline-1-one, B.p.$_{0.1}$ 110° to 112° C.

d. 4-n-butyl-1-(1-imidazolyl)-isoquinoline-hydrochloride:
Reaction analogous to 8d., from 4-n-butyl-1-chloroisoquinoline. M.p. 206° to 207° C.

EXAMPLE 12:

4-n-Butyl-1-(4-phenyllmidazole-1-yl)-isoquinoline-hydrochloride

Reaction analogous to 8d., from 4-n-butyl-1-chloroisoquinoline and 4(5)-phenylimidazole. M.p. 166° to 167° C.

EXAMPLE 13:

4-n-Hexyl-3;4-dihydro-2H-isoquinonline a. 4-n-Hexyl-3,4-dihydro-2H-isoquinoline-1-one:
Reaction analogous to 8a, from N-(2-phenyl-n-octyl)-carbamic acid ethyl ester, B.p.$_{0.5}$ 170° to 175° C.

b. 4-n-Hexyl-2H-isoquinoline-1-one:
Reaction analogous to 8b., from 4-n-hexyl-3,4-dihydro-2H-isoquinoline-1-one, M.p. 82° to 85° C.

c. 1-Chloro-4-n-hexylisoquinoline:
Reaction analogous to 8c., from 4-n-hexyl-2H-isoquinoline-1-one, B.p.$_{0.1}$ 119° to 123° C.

d. 4-n-Hexyl-1-(1-imidazolyl)-isoquinoline-hydrochloride:
Reaction analogous to athat of 1-chloro-4-n-hexylisoquinoline, M.p. 167° to 168° C.

EXAMPLE 14:

1-(2-Methylimidazole-1-yl)-4-phenylisoquinoline-hydrochloride

Reaction analogous to 8d., from 1-chloro-4-phenylisoquinoline and 2-methylimidazole, M.p. 243° to 244° C.

EXAMPLE 15:

1-(1-Imidazolyl)-4-phenylisoquinoline-oxalate 9.15 g (30 mmoles) of 3-chloro-1-(1-imidazolyl)-4-phenylisoquinoline in 100 ml of ethanol and 4.8 ml of triethylamine were hydrogenated at 60° C in a hydrogenating apparatus in the presence of 1 g of 10% Pd/BaSO$_4$. After about 3 hours, 1 mole of hydrogen was taken up and the hydrogenation stopped. After separation of the catalyst, the mixture was concentrated and the residue was taken up in ethyl acetate and water. The aqueous phase was again extracted with ethyl acetate and the combined ethyl acetate solutions were washed with water and dried over NaSO$_4$. The oxalate was precipitated with a solution of 3.0 g (33 mmoles) of oxalic acid in ethyl actate. Decomposition 220° C.

EXAMPLE 16:

3-Ethyl-1-(1-imidazolyl)-isoquinoline-hydrochloride a. 3-Ethylisoquinoline-1-one
88.3 g (0.87 mole) of triethylamine in 100 ml of absolute acetone were added dropwise to 128 g (0.73 mole) of 2-ethylcinnamic acid in 1200 ml of absolute acetone. The whole was stirred for 10 minutes and 94.6 g (0.87 mole) of chloroformic acid ethyl ester in 100 ml of absolute acetone were added dropwise with stirring. After 1 hour, a concentrated solution of 65 g (1 mole) of sodium azide in a small amount of water was added dropwise and stirring was continued for 30 minutes. The major part of the solvent was removed at room temperature under reduced pressure and the residue was poured onto ice. Extraction was effected with methylene chloride and the organic phase was washed with water and dried carefully over MgSC$_4$. This solution of the acid azide was added dropwise into 350 ml of boiling diphenyl ether, during which time the methylene chloride was simultaneously distilled off. The whole was further heated for 1 hour under reflux and then the solvent was removed under reduced pressure. The residue was recrystallized from ethanol. M.p. 139° to140° C.

b. 3-Ethyl-1-chlorisquinoline:
14 g (81 mmoles) of 3-ethylisoquinoline-1-one were heated under reflux in 50 ml of POCl$_3$ until thin-layer chromatagraphic analysis of the reaction mixture showed the end of the reaction. The mixture was concentrated under reduced pressure. The residue was poured onto ice and rendered alkaline with dilute sodium hydroxide solution. The product was extracted with methylene chloride and distilled after drying. B.p.$_{0.1}$ 101° to 104° C.

c. 3-Ethyl-1-(1-imidazolyl)-isoquinoline:
Reaction analogous to 8d., with 3-ethyl-1-chlorosioquinoline, M.p. 85° to 86° C; hydrochloride: M.p. 224° to 225° C.

EXAMPLE 17:

3-Ethyl-4-chloro-1-(1-imidazolyl)-isoquinoline a. 3-Ethyl-1,4-dichlorosioquinoline:

15 g (87 mmoles) of 3-ethylisoquinoline-1-one and 35.2 g (174 mmoles) of phosphorus pentachloride were heated for 4 hours to 110° – 120° C. Then, hydrolysis was carried out dropwise with ethanol, while cooling and the reaction mixture was distributed between water and benzene. After drying and evaporation of the organic phase, there remained a yellowish oil which was reacted without further purification.

b. 3-Ethyl-4-chloro-1-(1-imidazolyl)-isoquinoline
Reaction analogous to 8d., from 3-ethyl-1,4-dichloroisoquinoline, M.p. 115° C.
Phosphate M.p. 148° to 149° C.

EXAMPLE 18:

1-(1-imidazolyl)-3-phenyl-isoquinoline a. 3-Phenyl-2H-iisoquinoline-1-one:
Reaction analogous to 15a., from 2-phenyl-cinnamic acid. M.p. 195° to 196° C.

b. 1-Chloro-3-phenylisoquinoline:
Reaction analogous to 15 b., from 3-phenyl-2H-isoquinoline-1-one, M.p. 76° C.

c. 1-(1-imidazolyl)-3-phenyl-isoquinoline:
Reaction analogous to 8d., from 1-chloro-3-phenyl-isoquinoline, M.p. 141° to 142° C.
Oxalate M.p. 189° to 190° C.

EXAMPLE 19:

4-Chloro-1-(1-imidazolyl)-3-phenylisoquinoleine a. 1,4-Dichloro-3-phenylisoquinoline:
Reaction analogous to 16 a. from 3-phenyl-2H-isoquinoleine-1-one, M.p. 159° C.

b. 4-Chloro-1-(1-imidazolyl)-3-phenylisoquinoline:
Reaction analogous to 8d., from 1,4-dichloro-3-phenyl-isoquinoline, M.p 189° C.
Oxalate M.p. 181° to 182° C.

We claim:

1. A pharmaceutical composition having hypolipemic and hypoglycemic activity consisting essentially of a physiologically tolerable carrier and, as the essential active compound, about 3 to 200 mg/kg per daily dosage unit of a 1-(1-imidazolyl)-isoquinoline of the formula

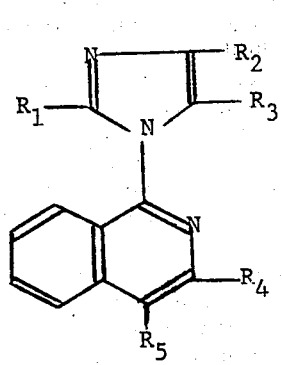

or a physicologically tolerated salt thereof, wherein $R_1$, $R_2$, and $R_3$, which may be the same or different, are hydrogen, alkyl of 1 to 4 carbon atoms, or phenyl, but $R_2$ and $R_3$ are not both alkyl; $R_4$ is hydrogen, alkyl of 1 to 4 carbon atoms, phenyl, or chlorine; and $R_5$ is hydrogen, alkyl of 1 to 6 carbon atoms, cycloalkyl of 5 to 8 carbon atoms, phenyl, or chlorine, but $R_4$ and $R_5$ are not both t-alkyl.

2. The composition defined in claim 1 in which the active compound is 3-chloro-1-(1-imidazolyl)-4-phenylisoquinoline or a physiologically tolerated salt thereof.

3. The composition defined in claim 1 in which the active compound is 3-chloro-1-(4,5-dimethylimidazolyl-1-yl)-4-phenylisoquinonline or a physiologically tolerated salt thereof.

4. The composition defined in claim 1 in which the active compound is 3-chloro-1(4,5-diphenylimidazole-1-yl)-4-phenylisoquinoline or a physioligcally tolerated salt thereof.

5. The composition defined in claim 1 in which the active compound is 3-chloro-1-(1-imidazolyl)-isoquinoline or a physiologically tolerated salt thereof.

6. The composition defined in claim 1 in which the active compound is 4-n-butyl-1-(1-imidazolyl)-isoquinoline or a physiologically tolerated salt thereof.

7. The composition defined in claim 1 in which the active compound is 4-ethyl-1-(1-imidazolyl)-isoquinoline or a physiologically tolerated salt thereof.

8. The composition defined in claim 1 in which the active compound is 4-phenyl-1-(1-imidazolyl)-isoquinoline or a physiologically tolerated salt thereof.

9. The composition definded in claim 1 in which the active compound is 3-chloro-1-(2-methylimidazole-1-yl)-4-phenylisoquinoline or a physiologically tolerated salt thereof.

10. A method for the treatment of hyperlipemia in a patient which comprises administering to said patient a daily dosage of about 3 to 200 mg/kg of an active compound of the formula

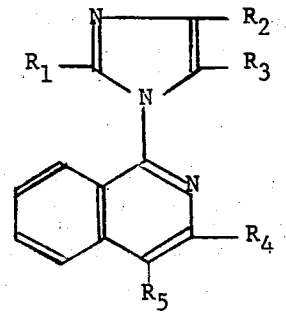

or a physiologically tolerated salt thereof, wherein $R_1$, $R_2$, and $R_3$, which may be the same or different, are hydrogen, alkyl of 1 to 4 carbon atoms, or phenyl, but $R_2$ and $R_3$ are not both t-alkyl; $R_4$ is hydrogen, alkyl of 1 to 4 carbon atoms, phenyl, or chlorine; and $R_5$ is hydrogen, alkyl of 1 to 6 carbon atoms, cycloalkyl of 5 to 8 carbon atoms, phenyl, or chlorine, but $R_4$ and $R_5$ are not both t-alkyl.

11. The method defined in claim 10 in which the active compound is 3-chloro-1-(1-imidazolyl)-4-phenylisoquinoline or a physiologically tolerated salt thereof.

12. The method defined in claim 10 in which the active compound is 3-chloro-1-(4,5-dimethylimidazolyl-1-yl)-4-phenylisoquinoline or a physiologically tolerated salt thereof.

13. The method defined in claim 10 in which the active compound is 3-chloro-1-(4,5-diphenylimidazolyl-1-yl)-4-phenylisoquinoline or a physiologically tolerated salt thereof.

14. The method defined in claim 10 in which the active compound is 3-chloro-1-(1-imidazolyl)-isoquinoline or a physiologically tolerlated salt thereof.

15. The method defined in claim 10 in which the active compound is 4-n-butyl-1-(1-imidazolyl)-isoquinoline or a physiologically tolerated salt thereof.

16. The method defined in claim 10 in which the active compound is 4-ethyl-1-(1-imidazolyl)-isoquinoline or a physiologically tolerated salt thereof.

17. The method defined in claim 10 in which the active compound is 4-phenyl-1-(1-imidazolyl)-isoquinoline or a physiologically tolerated salt thereof.

18. The method defined in claim 10 in which the active compound is 3-chloro-1-(2-methylimidazole-1-yl)-4-phenylisoquinoline or a physiologically tolerated salt thereof.

* * * * *

UNITED STATES PATENT AND TRADEMARK OFFICE
CERTIFICATE OF CORRECTION

PATENT NO. : 3,961,062
DATED : June 1, 1976
INVENTOR(S) : Lerch et al.

It is certified that error appears in the above-identified patent and that said Letters Patent are hereby corrected as shown below:

In the Heading, Item [30], replace "231498" by --2314985--.

Signed and Sealed this

Tenth Day of August 1976

[SEAL]

Attest:

RUTH C. MASON
Attesting Officer

C. MARSHALL DANN
Commissioner of Patents and Trademarks